(12) United States Patent
Gangadhar

(10) Patent No.: US 7,774,185 B2
(45) Date of Patent: Aug. 10, 2010

(54) PROTEIN STRUCTURE ALIGNMENT USING CELLULAR AUTOMATA

(75) Inventor: Deepak K Gangadhar, Karnataka (IN)

(73) Assignee: International Business Machines Corporation, Armonk, NY (US)

( * ) Notice: Subject to any disclaimer, the term of this patent is extended or adjusted under 35 U.S.C. 154(b) by 1340 days.

(21) Appl. No.: 10/940,192

(22) Filed: Sep. 14, 2004

(65) Prior Publication Data

US 2006/0058968 A1 Mar. 16, 2006

(51) Int. Cl.
G06G 7/48 (2006.01)
G01N 33/48 (2006.01)
G01N 31/00 (2006.01)
G06F 19/00 (2006.01)

(52) U.S. Cl. .............................. 703/11; 702/19; 702/22; 702/27

(58) Field of Classification Search .................. None
See application file for complete search history.

(56) References Cited

U.S. PATENT DOCUMENTS

| | | | |
|---|---|---|---|
| 5,288,615 | A | 2/1994 | Lee et al. |
| 5,453,937 | A | 9/1995 | Srinivasan et al. |
| 6,579,710 | B2 | 6/2003 | Turner, Jr. et al. |
| 2002/0111781 | A1 | 8/2002 | Blankenbecler et al. |
| 2002/0132998 | A1 | 9/2002 | Friddle et al. |

OTHER PUBLICATIONS

Xu et al. "Protein Structure Determination using Protein Threading and Sparse NMR Data", RECOMB (2000), pp. 299-307.*
Burley, Stephen K., "*An overview of Structural Genomics*", Nature Structural Biology, Structural Genomics Supplement, Nov. 2000, pp. 932 to 934.
Singh, Amit P. and Brutlag, D.L., "*Protein Structure Alignment: A Comparison of Methods*", Stanford University, CA, 2000 (available from http://citeseer.ist.psu.edu/390690.html).
Wolfram, S., "*Cellular Automata as Simple Self-Organizing System*", 1982, Caltech preprint CALT—-68-938.
Packard, N.H. and Wolfram, S.,"*Two-Dimensional Cellular Automata*", Journal of Statistical Physics, Mar. 1985, vol. 38, pp. 901-946.
Krasnogor, N., Marcos, D.H., Pelta D., Risi, W.A., "*Protein Structure Prediction as a Complete Adaptive Array*", Proc. 4th Joint Conference on Intelligent Systems 1999 (JCIS '98), Research Triangle Park, NC, USA, Oct. 1998, vol. 2, pp. 441-447.
Gaasterland, T., Karp, P., Karplus, K., Ouzonis, C., Sander, C., Valencia, A., Inspec Assession No. 6269875, 1997.
Sharmir, R., Miyano, S., Istrail, S., Peuzner, P., Waterman, M., Inspec Assession No. 7028826, 2000.
Tyson, H., Fieldes, M.A., Inspec Assession No. 4294422, 1992.
Bailey-Kellogg, C., Widge, A., Kelley, J.J., Berardi, M.J., Bushweller, J.H., Donald, B.R., "*The NOESY Jigsaw: Automated Protein Secondary Structure and Main-Chain Assignment from Sparse, Unassigned NMR Data*"., Proc. RECOMB 2000, Tokyo, Japan, pp. 33-44.
Hameroff, S.R., Dayhoff, J.E., Lahoz-Beltra, R., Samsonovich, A.V., Rasmussen, S., "*Models for Molecular Computation: Conformational Automata in the Cytoskeltan*", IEEE Computer, Nov. 1992, pp. 30-39.
Holm, Liisa, Sander, Chris, "*Protein Structure Comparison by Alignment of Distance Matrices*", 1993, J. Mol. Biol. 233: pp. 123-138.

* cited by examiner

*Primary Examiner*—Eric S Dejong
(74) *Attorney, Agent, or Firm*—Anthony V S England; William H. Steinberg

(57) ABSTRACT

The detection of protein sequence alignments firstly generates protein blocks having n successive C-alpha atoms from two protein sequences. A matrix of the distance of protein atoms from said C-alpha atoms for each block is then determined. A difference matrix is determined from respective distance matrices representing the differences between the protein blocks of the two protein structures. A Cellular Automaton (CA) model is generated in an initial configuration based upon the difference matrix, and evolved through at least one generation using predetermined rules. The rules determine which CA cells remain live and which are set to be dead.

24 Claims, 13 Drawing Sheets

$$P1_1 = \begin{pmatrix} 0.0 & 1.3 & 2.4 & 3.2 & 4.2 \\ 1.3 & 0.0 & 1.5 & 2.9 & 3.6 \\ 2.4 & 1.5 & 0.0 & 1.1 & 2.1 \\ 3.2 & 2.9 & 1.1 & 0.0 & 0.9 \\ 4.2 & 3.6 & 2.1 & 0.9 & 0.0 \end{pmatrix}$$

FIGURE 3A

$$P2_1 = \begin{pmatrix} 0.0 & 1.1 & 2.2 & 4.2 & 5.2 \\ 1.1 & 0.0 & 2.5 & 3.9 & 4.6 \\ 2.2 & 2.5 & 0.0 & 2.1 & 3.1 \\ 4.2 & 3.9 & 2.1 & 0.0 & 1.2 \\ 5.2 & 4.6 & 3.1 & 1.2 & 0.0 \end{pmatrix}$$

FIGURE 3B

|        | $P2_1$ | $P2_2$ | $P3_3$ | $P2_4$ | $P2_5$ | ... |
|--------|--------|--------|--------|--------|--------|-----|
| $P1_1$ | 15.4   | 2.9    | 3.6    | ...    | ...    | ... |
| $P1_2$ | 2.4    | 0.9    | ...    | ...    | ...    | ... |
| $P1_3$ | 1.8    | ...    | ...    | ...    | ...    | ... |
| $P1_4$ | ...    | ...    | ...    | ...    | ...    | ... |
| $P1_5$ | ...    | ...    | ...    | ...    | ...    | ... |
| ...    |        |        |        |        |        |     |

FIGURE 4

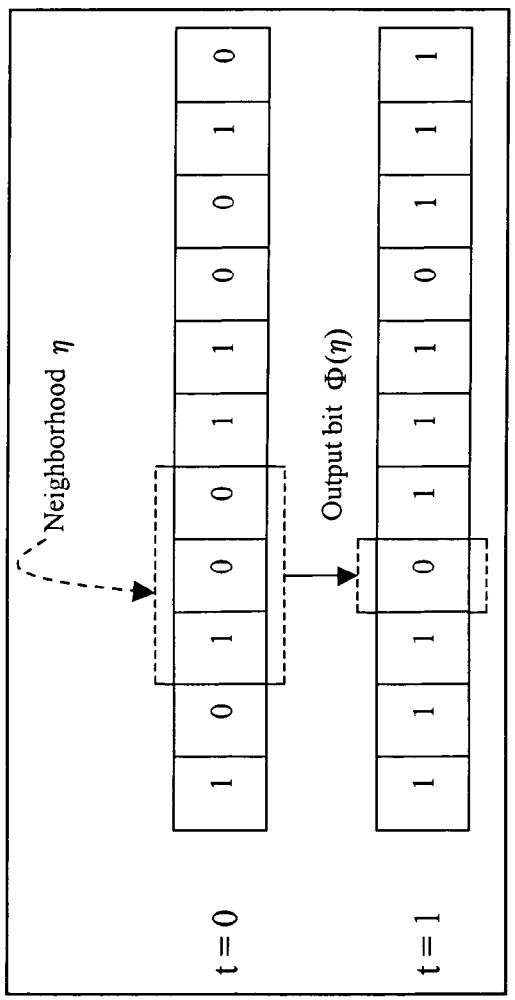
FIGURE 5
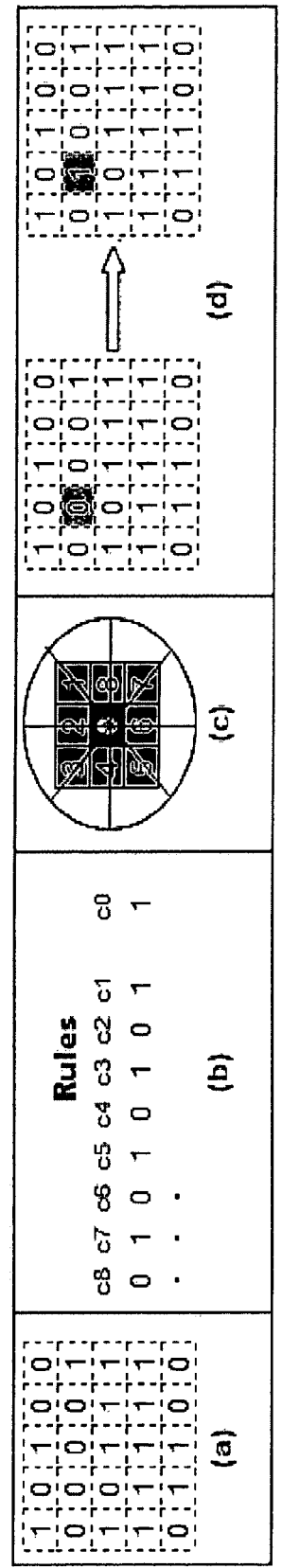
FIGURE 6A
FIGURE 6B
FIGURE 6C
FIGURE 6D

|  |  |  |  |  |  |
|---|---|---|---|---|---|
| 1.1 | 0.3 | 2.1 | 1.8 | 1.9 | 1.9 |
| 6.1 | 3.8 | 0.2 | 1.8 | 3.3 | 1.3 |
| 2.1 | 9.0 | 2.1 | 0.1 | 2.2 | 1.2 |
| 1.1 | 3.1 | 9.5 | 7.3 | 0.2 | 9.2 |
FIGURE 7A
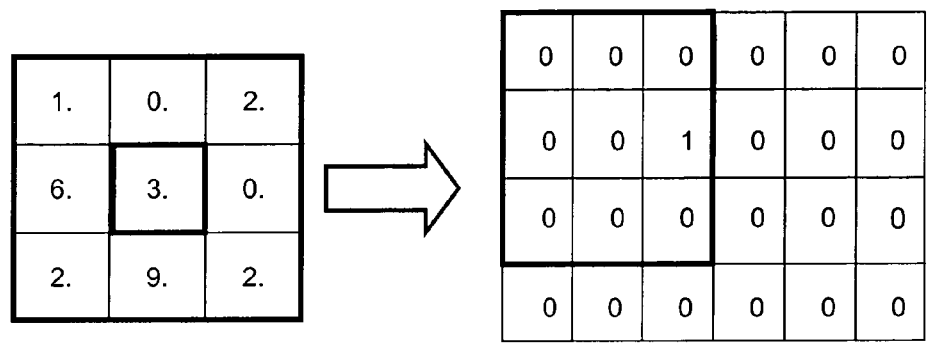
FIGURE 7B
|  |  |  |  |  |  |
|---|---|---|---|---|---|
| 0 | 0 | 0 | 0 | 0 | 0 |
| 0 | 0 | 1 | 0 | 0 | 0 |
| 0 | 0 | 0 | 1 | 0 | 0 |
| 1 | 0 | 0 | 0 | 1 | 0 |
FIGURE 7C
FIGURE 7D

FIGURE 9

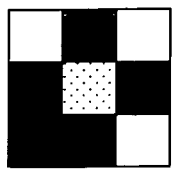
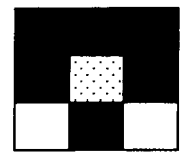
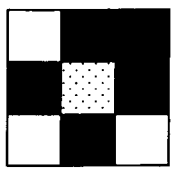
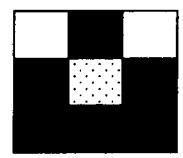
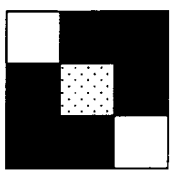
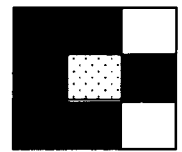
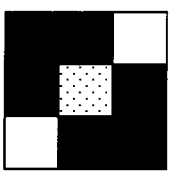
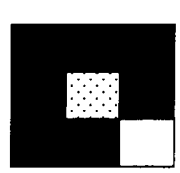
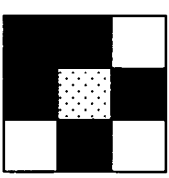
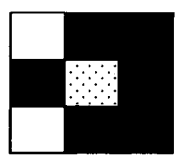
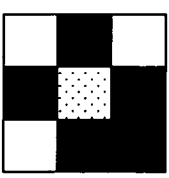
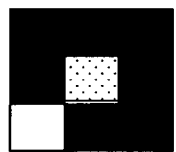
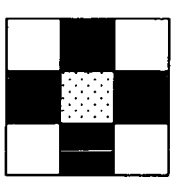
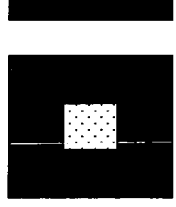
FIGURE 10A            FIGURE 10B

US 7,774,185 B2

PROTEIN STRUCTURE ALIGNMENT USING CELLULAR AUTOMATA

FIELD OF THE INVENTION

The present invention relates to protein structure alignment using cellular automata.

BACKGROUND

At the end of the year 2003 more than 23,000 protein structures had been deposited in the Protein Data Bank (PDB), with more structures being discovered with each passing day. This surge in structure information has lead researchers to look out for efficient techniques to compare protein structures, detect motifs, classify proteins under specific families, etc.

While the current dogma of genetics connecting sequences to structures (sequence→structure→function) suggests that it would suffice if sequences were studied in greater details to detect similarity in proteins and classify them, there are several instances when different sequences yield the same structure. Hence there is a concerted effort to work with the 3-dimensional structure of proteins directly.

With all this structural information overflow emerges new necessities: that of identifying similar structures and mapping them to families, a quick and fast way to detect similarity, identify motifs, find longest contiguous alignments, etc.

Distance matrices are known to be used for various protein structure-related work. DALI (proposed by Holm and Sander) is a well-known structure alignment algorithm utilizing the concept of distance matrices. In DALI, the three-dimensional coordinates of each protein are used to calculate residue-residue ($C^{alpha}$-$C^{alpha}$) distance matrices. The distance matrices are first decomposed into elementary contact patterns, e.g., hexapeptide-hexapeptide submatrices. Then, similar contact patterns in the two matrices are paired and combined into larger consistent sets of pairs. A Monte Carlo procedure is used to optimise a similarity score defined in terms of equivalent intramolecular distances. Several alignments are optimised in parallel, leading to simultaneous detection of the best, second-best and so on solutions.

A need exists, however, for an improved manner of processing protein structure information.

SUMMARY

A protein alignment detection system uses an algorithm incorporating Cellular Automaton (CA) models for obtaining pairwise structure alignment of two proteins. Two-dimensional CA models are used, and the alignment information is presented in the form of patterns formed by the cells of the CA.

Breaking down the protein structure into distance matrices of 5 peptide units (Penta Peptide Blocks), the described system uses the differences of these matrices to construct the 2-dimensional CA grid. Each cell in the CA grid corresponds to an alignment with the state of the cell (dead or alive) indicating the presence or absence of an alignment at that location as determined from the state of the surrounding cells. Starting from an initial unaligned state, the CA evolves through several generations according to a defined set of local rules. The emergent pattern, as the CA evolves through successive generations, yields the alignment.

The described system exhibits "emergent" behaviour. Each cell behaves in a strictly microscopic way, but each individual cell's behaviour leads to a macroscopic long range behaviour exhibited by the entire system, which collectively indicates the alignment.

DESCRIPTION OF DRAWINGS

FIGS. 3A and 3B are the distance matrices for two protein structures.

FIG. 4 is the difference matrix computed from the PPB of the two proteins of FIGS. 3A and 3B.

FIG. 5 shows an elementary CA iterated over one time step.

FIGS. 6A-6D show the components of a 2-dimensional CA.

FIGS. 7A-7D show a schematic representation of the generation of a cellular automation (CA) from a difference matrix.

Figure 9:
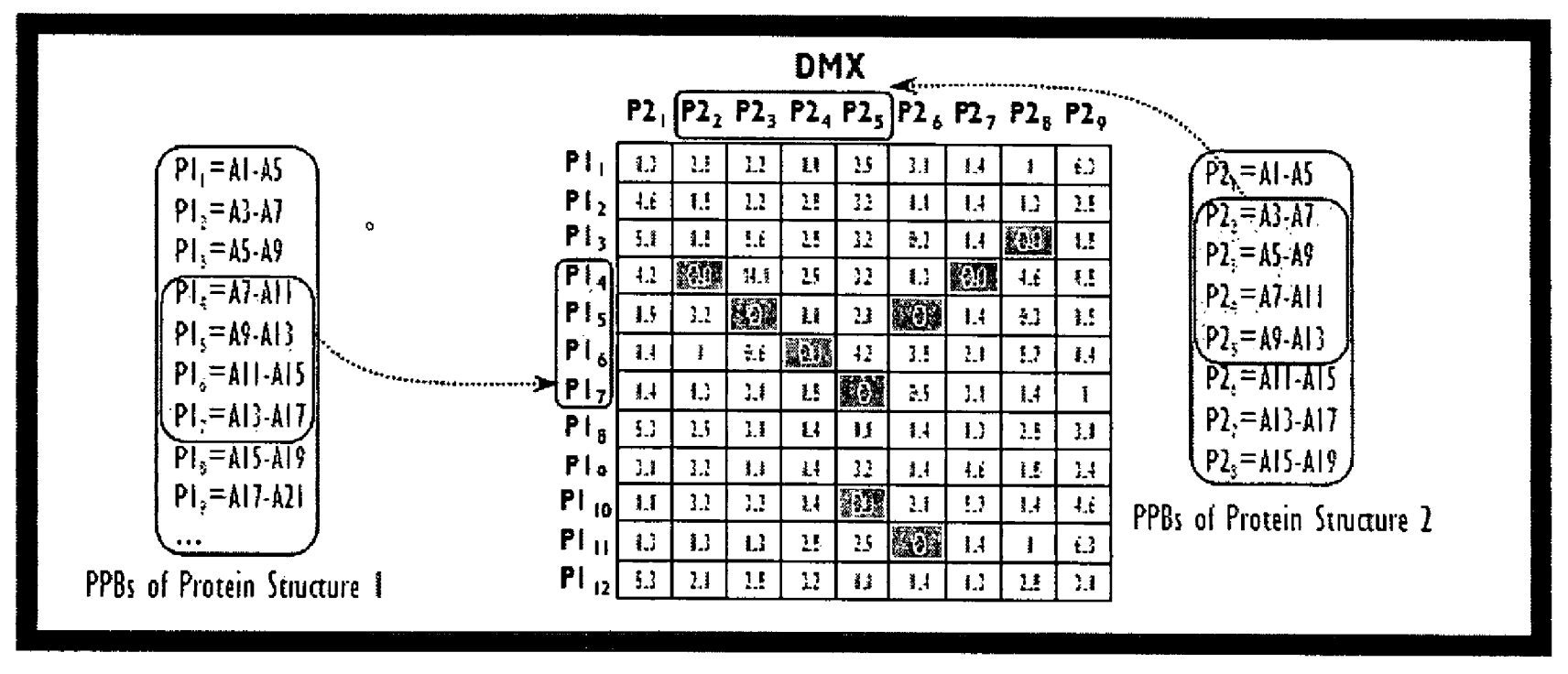

FIG. 9 shows a difference matrix for the protein structures of FIGS. 8A and 8B.

FIGS. 10A and 10B is a schematic representation of neighboring units for which the centre unit lives, and FIG. 10B is a representation of neighboring unit configurations for which the central unit dies.

DETAILED DESCRIPTION

Overview

Figure 1:
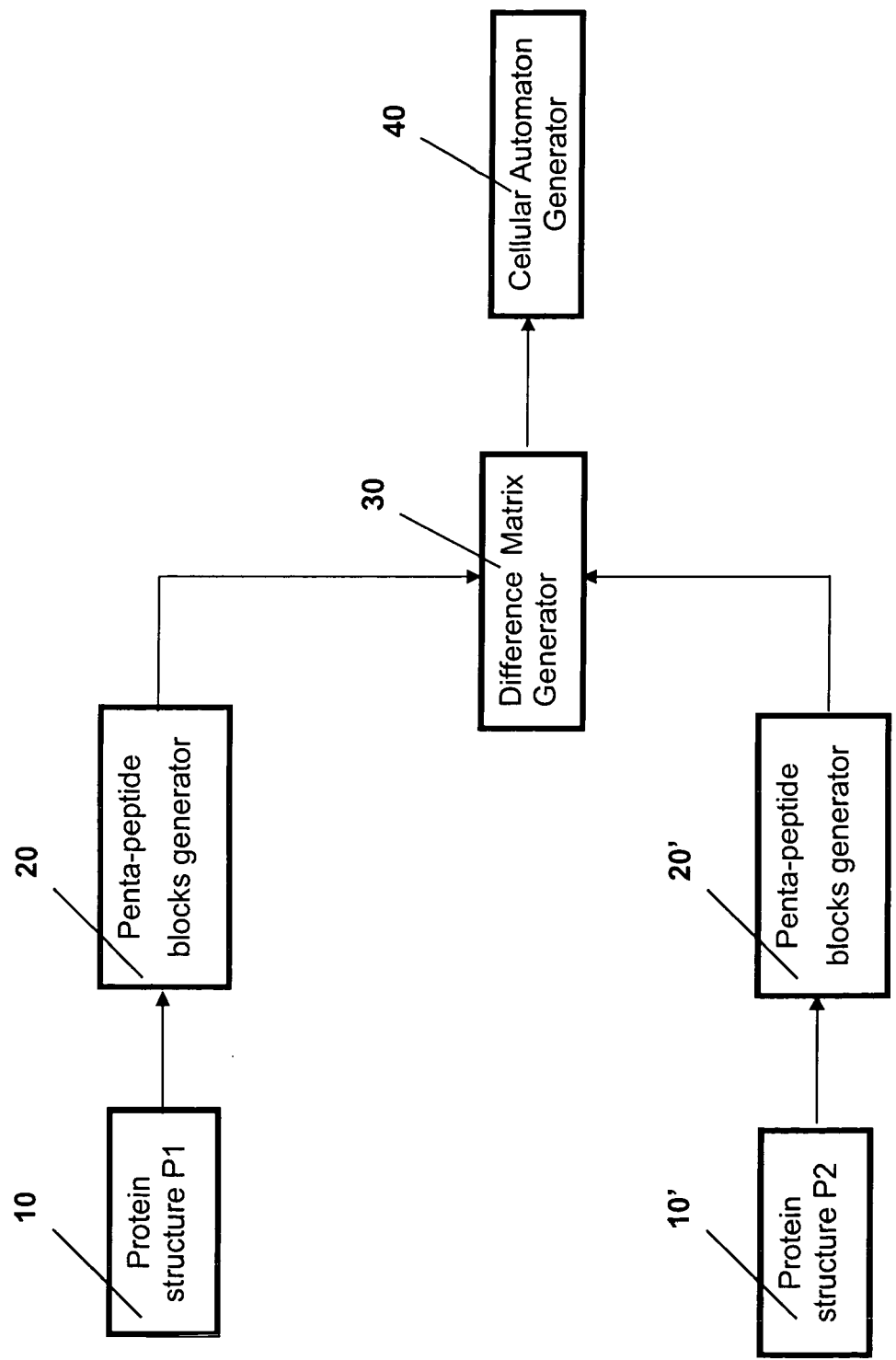
FIG. 1 is a schematic representation of a protein alignment detection system incorporating cellular automaton (CA) models.

FIG. 1 schematically represents the operation of the protein alignment detection system described herein. Two protein structures P1 10 and P2 10', which are to be aligned, are both deconstructed to smaller units [$P1_1$, $P1_2$, ... and $P2_1$, $P2_2$, ...] by a respective PPBs generator 20, 20'. Each of the protein sub-units (P1, P2) comprise n successive C-alpha atoms of the primary amino acid sequence. An appropriate value of n is selected. The PPB generators 20, 20' then compute the distance matrix of each PPB by determining the distance between protein atoms from the atom's C-alpha position.

For the given two protein structures, a Difference Matrix (DMX) is computed from the respective distance matrices by a generator 30.

A CA generator 40 uses the DMX to generate an initial configuration of a 2-dimensional CA. The CA model evolves through several generations according to a pre-defined set of microscopic rules. The rules are designed so that only cells corresponding to the longest alignments of the two structures survive.

Selection of Number of C-Atoms (n)

Distance Matrices are a suitable technique for structure comparisons and alignments. There are a range of values that can be used for the protein sub-units. Choosing a value of "1" would not serve the purpose, because that would mean that the algorithm is dealing with individual points and there is no concept of a distance, bringing with it the problems of rotation, translation, etc. Any n>1 would be appropriate. On the other hand, choosing too high a value would mean that if there are motifs comprising of, say, 10 amino acid sequences, they would get lost in the resultant huge matrix since the difference matrix generation wouldn't give a low difference. Small structural details like loops and bends can be detected if n<10. The value of n is selected as being 5.

Distance Matrix

Figure 2:
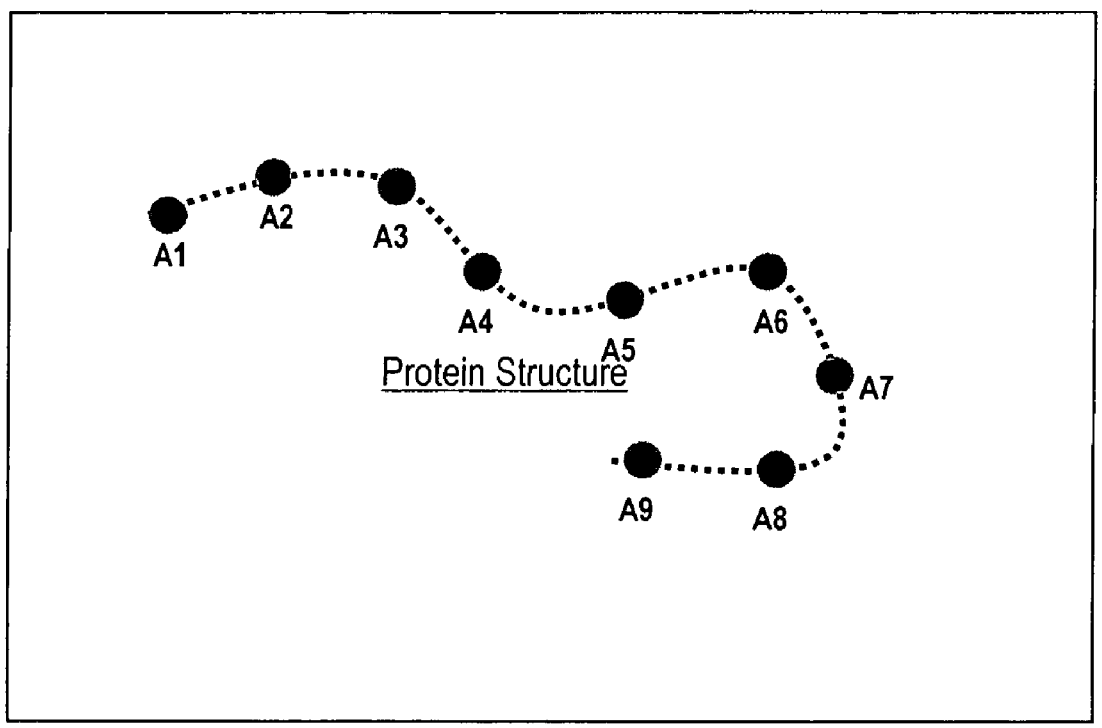
FIG. 2 is a schematic of a protein structure.

The Penta Protein Block (PPB) of a protein structure is denoted by $Pi_j$, where i is the protein index and j is the PPB number. The set of PPBs for a protein structure P1 shown in FIG. 2 is:

PPB1=[A1, A2, A3, A4, A5]

PPB2=[A3, A4, A5, A6, A7]

PPB3=...

The protein structure P2 is not shown.

If A1 and A2 are the amino acids of a protein structure with their C-alpha positions given as A1 $(X_1, Y_1, Z_1)$ and A2 $(X_2, Y_2, Z_2)$, then the distance between them is constructed as:

$$D_{12}=\sqrt{((x_2-x_1)^2+(y_2-y_1)^2+(z_2-z_1)^2)} \quad [1]$$

The distance matrix $P1_1$ for protein structure P1 is shown in FIG. 3A. The distance matrix $P2_1$ for protein structure P2 is shown in FIG. 3B. Both have been calculated by equation [1].

Difference Matrix

The difference matrix DMX is a (m,n) matrix given by:

$$DMX_{ij}=\Sigma|P1_i-P2_j| \text{ for } i=1 \ldots m \text{ and } j=1 \ldots n \quad [2]$$

FIG. 4 provides an explanation of equation [2] with an example of how the first cell of the DMX is calculated. $DMX_{11}$ is the sum of the absolute differences of each element of $P1_1$ and $P2_1$:

$$DMX_{11}=|0.0-0.0|+|1.3-1.1|+|2.4-2.2|+|3.2-4.2|+|4.2-5.2|\ldots$$
$$|4.2-5.2|+|3.6-4.6|+|2.1-3.1|+|0.9-1.2|+|0.0-0.0|=15.4$$

Similarly, $DMX_{12}$ would be calculated using $P1_1$ and $P2_2$, and so on, till all elements of the DMX are calculated. The completed DMX provides the basis for generating the initial configuration of the Cellular Automata.

Cellular Automata

Cellular Automata (CA) are a simple class of systems that exhibit the following characteristics.

Large number of homogenous components (simple finite state machines)
Extended in space
Absence of central control
Limited communication among components.

A one-dimensional CA consists of a lattice of N identical finite state machines (cells) each with an identical topology of local connections to other cells for input and output. Each cell is indexed by its site number i=0, 1, 2 ... N−1. A cell's state at time t is give by $s^t_i$. The state $s^t_i$ of cell i together with the states of the cells to which it is connected is called the neighborhood $n^t_i$ of the cell i. Each cell obeys the same transition rule Φ, that gives the updated state $s^{t+1}_i=\Phi(n^t_i)$ for cell I as a function of $n^t_i$.

For a 1-dimensional CA, the rule table is:

TABLE 1

| Neighborhood η: | 000 | 001 | 010 | 011 | 100 | 101 | 110 | 111 |
|---|---|---|---|---|---|---|---|---|
| Output bit Φ (η): | 0 | 1 | 1 | 1 | 0 | 1 | 1 | 0 |

FIG. 5 shows the components of a one-dimensional, binary state, r=1, elementary CA shown iterated one time step.

A 2-dimensional CA has a grid of cells as opposed to a single row of cells as in the case of a 1-dimensional CA. FIGS. 6A-6D shows the components of a 2-dimensional CA in greater detail.

FIG. 6A shows the initial configuration (IC) of the CA. The IC is the entire population of cells (both dead and alive) with which the CA starts evolving according to the defined rules. Cells may be dead (indicated by the value 0) or alive (indicated by the value 1). Cells may have other values in case of non-binary CA. In binary CA, however, "0" and "1" are the only permitted values.

FIG. 6B shows one of the rules of the CA. This rule says that if the c1, c3, c5 and the c7 neighbors of a cell are alive in any generation, then this cell lives in the next generation. There will be many such rules indicating the various possibilities of the neighbors' states and the states of the cell itself. This is an illustrative example showing only one such rule. In fact, there will be a total of $2^8$=256 such rules.

As shown in FIG. 6C, each cell has 8 neighbors marked 1-8 (this is also called the 9-neighbor square). The cell itself is marked 0. In light of this, the previous rule states that if cells 1, 3, 5 and 7 are alive, then the cell marked 0 is alive in the next generation.

Finally in FIG. 6D, the CA evolves from its initial configuration to its first generation. Shown is a cell which is dead in the initial configuration. Now, when the CA evolves into the next generation, the update rules are checked. One such rule says that if the 1, 3, 5, 7 cells are alive, then that cell lives. In this example, this rule is satisfied and so the cell becomes alive in the subsequent generation, as shown.

Generation of Cellular Automata

The Difference Matrix generator 30 takes the difference matrix and using the values of the matrix, transforms it into the initial configuration (IC) of the CA.

FIG. 7A shows the sample DMX. Each element in the DMX acts as a cell. The neighbors of each cell are examined to find the minimum among them and these neighbors are made alive. Consider the cell with value 3.8. The first grid in FIG. 7B shows the neighbors of the '3.8 cell' and it can be seen that the minimum value neighbor is that with a value of 0.2. The second grid in FIG. 7B shows the live cell and its place in the overall IC.

This process is performed for each cell within the DMX to give the complete IC. The grid in FIG. 7C shows the completed IC, whereas FIG. 7D shows another representation, where dead cells (value-0) are marked black and live cells (value-1) marked white.

Alignment Principle

All alignments (significant or otherwise) between the two protein structures will be visible in the Difference Matrix. Patterns thus need to be identified.

Figure 8B:
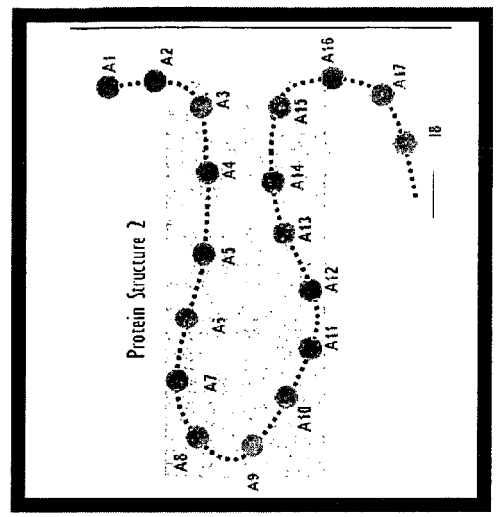
FIGS. 8A and 8B show two sample protein structures.
Figure 8A:
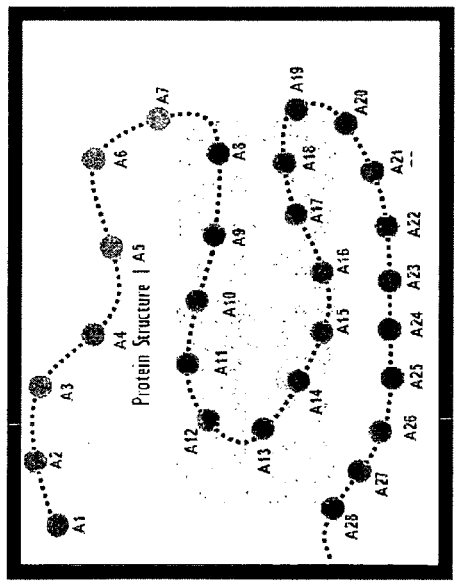

FIGS. 8A and 8B are protein structures, and the shaded portions of the protein structures are evidently similar. The PPBs of protein structure 1 are:

$P1_1=A1-A5, P1_2=A3-A7, P1_3=A5-A9,$ $P1_4=a7-A11, P1_5=A9-A13, P1_6=A11-A15,$ $P1_7=A13-A17, P1_8=A17-A21,\ldots$ The PPBs of protein structure 2 are:

$P2_1=A1-A5, P2_2=A3-A7, P2_3=A5-A9,$ $P2_4=A7-A11, P2_5=A9-A13, P2_6=A11-A15,$ $P2_7=A13-A17, P2_8=A15-A19,\ldots$ The DMX is computed and is shown in FIG. 9. The similar structures correspond to:

A7 to A18 of protein structure 1 (corresponding to $P1_4$ to $P1_7$ PPBs), and

A3 to A15 of protein structure 2 (corresponding to $P2_2$ to $P2_5$ PPBs).

Looking at the DMX, it is evident that there will be a contiguous run of diagonal cells of low value corresponding to the alignment because the distance matrices will be similar at these locations. The location of these low valued cells will be corresponding to the locations of $P1_4$ to $P1_7$ against $P2_2$ to $P2_5$.

Notice from the DMX in FIG. 9 that alignment patterns can be formed as cross-diagonals running in either direction (i.e. either in "3-7" or the "1-5" directions, as defined in FIG. 6C).

It is evident in FIG. 9 that the long diagonal running in 3-7 direction comprises an alignment. The objectives of alignment are to:

Eliminate all spurious alignments;
Retain the largest contiguous alignments; and
Indicate the direction of the alignments.

CA Rules for Continuous Alignment

Detecting the significant contiguous alignments involves designing a set of rules using which, in use, causes the CA to evolve and in the process eliminate all other cells that are not part of the alignment. Instead of looking at all the eight neighbors of a cell for writing the rules, only the cross neighbors are of importance. The guiding rule is that a cell that is alive should remain alive into the next generation if and only if cross neighbors along one or both directions are alive, i.e. either the "1-5" or the "3-7" direction (refer again to FIG. 6C for the definition of these directions). Applying these rules successively to all the cells of a particular generation should eliminate all such cells that are not part of the alignment. FIG. 10A shows all possible cross-neighbor combinations for which the centre cell lives, while FIG. 10B shows the remaining cells with states not found in FIG. 10A that will die.

Figure 11:
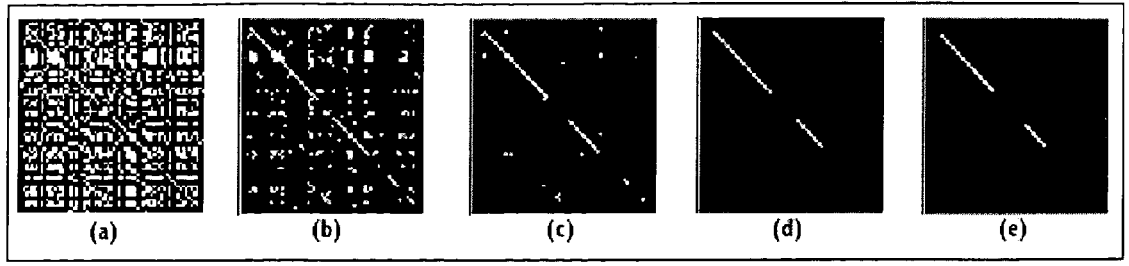
FIG. 11 shows an initial protein structure configuration and 4-generation iteration of a difference matrix.
Figure 12:
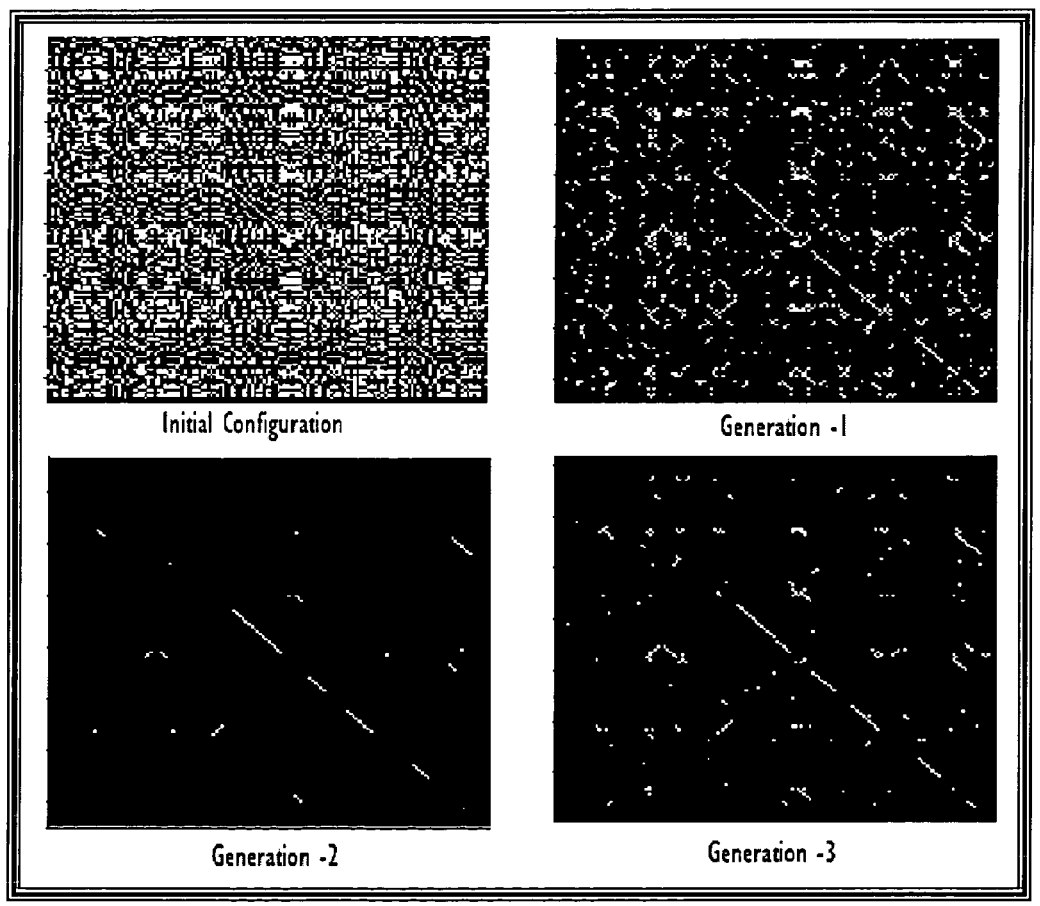
FIGS. 12-15 show the iterative protein structure over 3 generations for different protein-pairs.
Figure 13:
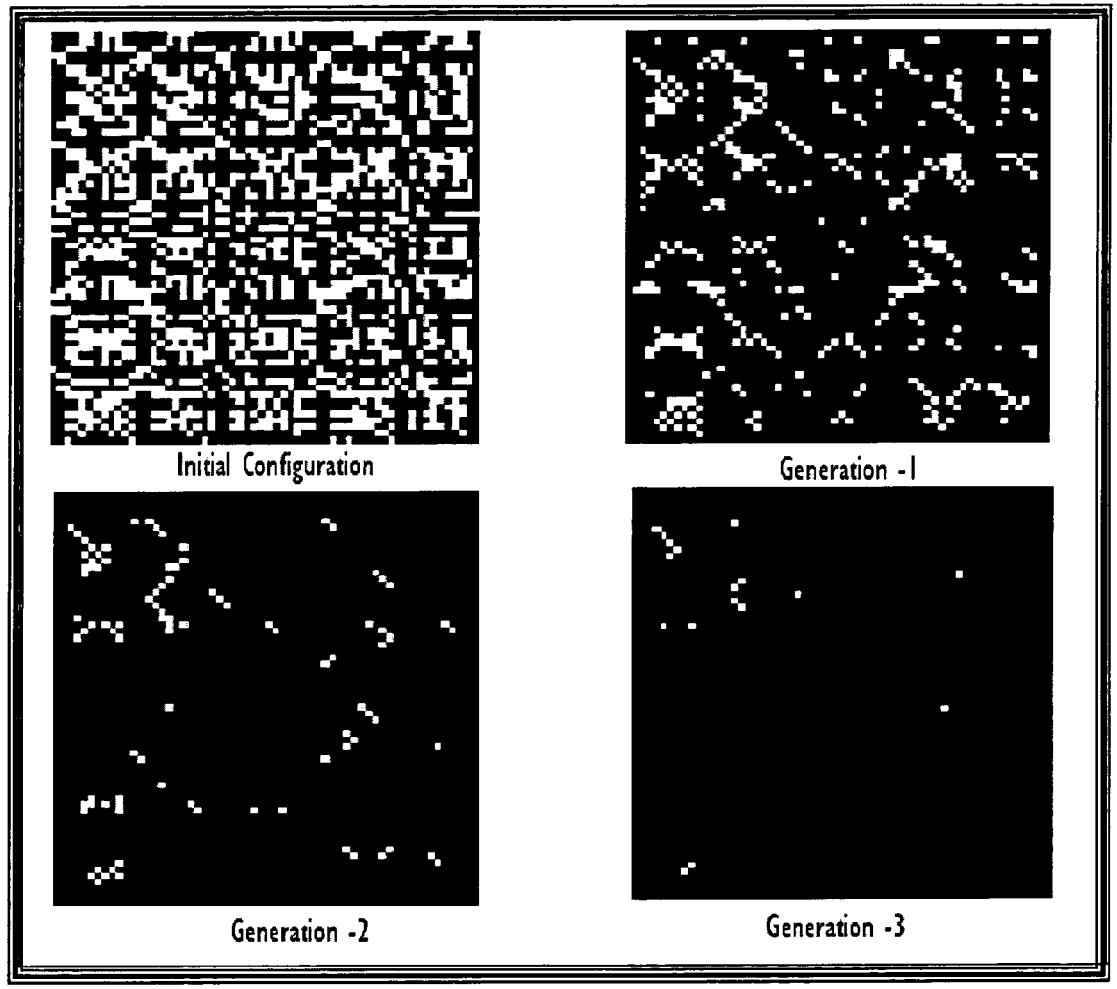
Figure 14:
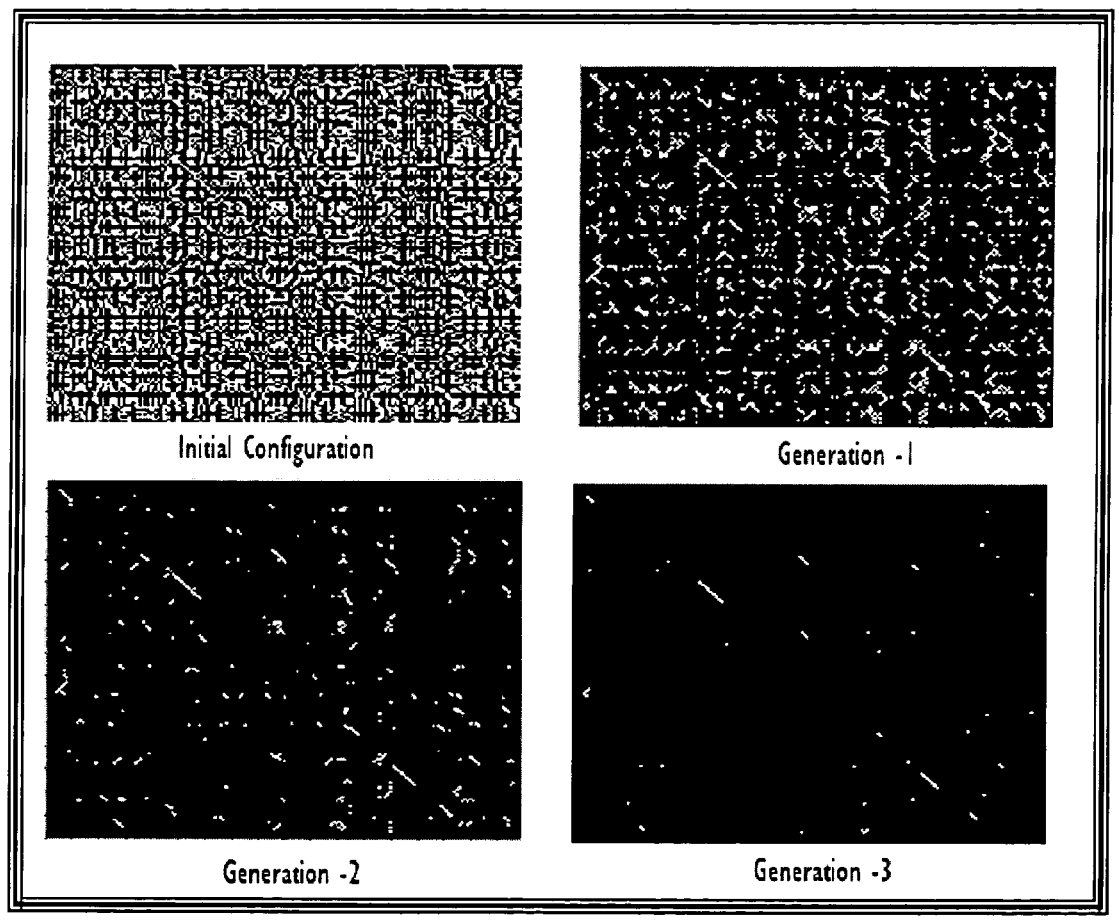
Figure 15:
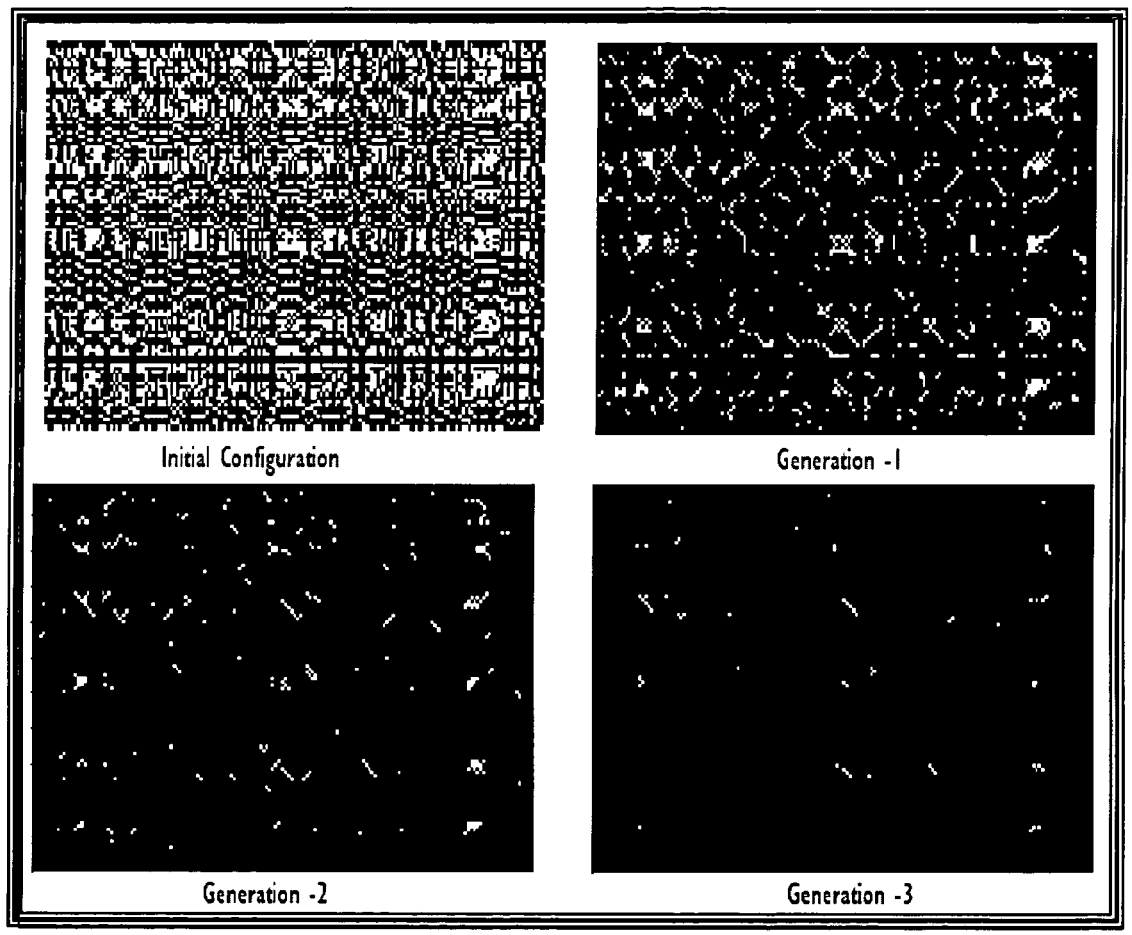

FIG. 11 shows a CA initial configuration of the "1a4f_A" and "1c40_A" protein structures and the same after the CA has evolved for 4 generations ((a)-(d)). As the CA evolved through several generations starting from the initial configuration, only those cells that contribute to an alignment survive and the rest of the cells are dead.

It can be observed that only those cells contributing to the alignment of similar structures survive in the final generations. At the same time, the live cells at the ends of the largest alignment are successively getting eliminated. However, this is not a cause of concern because the survival of a lone live cell (a cell without any live neighbors) in the nth generation implies that it is part of an alignment that is at least of length 2n+1 (n cells on either direction plus itself).

Directions of Alignment

There could be more than one direction of alignment according to the alignment principle. It is possible that a cell contributes to an alignment in the 3-7 direction and in the 1-5 direction. In such cases, a non-binary CA is utilised. A cell is considered as alive if it has a value greater than 1, the state of a cell is set according to the following table:

TABLE 2

| 1-5 | 3-7 | Value | state |
| --- | --- | --- | --- |
| 0 | 0 | 0 | dead |
| 0 | 1 | 1 | alive |
| 1 | 0 | 2 | alive |
| 1 | 1 | 3 | alive |

In view of this, the final cross-neighbor update rules, combining the information of Table 2 and FIGS. 10A and 10B are:

TABLE 3

| c7 | c5 | c3 | c1 | c0 |
| --- | --- | --- | --- | --- |
| 0 | 0 | 0 | 0 | 0 |
| 0 | 0 | 0 | 1 | 0 |
| 0 | 0 | 1 | 0 | 0 |
| 0 | 0 | 1 | 1 | 0 |
| 0 | 1 | 0 | 0 | 0 |
| 0 | 1 | 0 | 1 | 1 |
| 0 | 1 | 1 | 0 | 0 |
| 0 | 1 | 1 | 1 | 2 |
| 1 | 0 | 0 | 0 | 0 |
| 1 | 0 | 0 | 1 | 0 |
| 1 | 0 | 1 | 0 | 1 |
| 1 | 0 | 1 | 1 | 2 |
| 1 | 1 | 0 | 0 | 0 |
| 1 | 1 | 0 | 1 | 1 |
| 1 | 1 | 1 | 0 | 2 |
| 1 | 1 | 1 | 1 | 3 |

Also the value of a cell need not be the same across all generations. For instance, a cell will have a value 3 in the first generation, but in the next generation, it will have a value 1 because its neighbors will be dead in that generation. The longest alignments in any direction are tracked using this technique. Finally, only the cells of the longest alignments will survive.

Extensions

1. The algorithm discussed till now considers aligning the two structures without gaps. By a variation which involves considering the plus-neighbors and altering the update rules to maintain a gap cell to be live into the subsequent generations, the algorithm can also align structures with gaps.
2. The algorithm can be run with two sets of PPBs for one of the protein structures. The PPB Generator 20 would skip the first Amino Acid and generate blocks starting from the second Amino Acid so that all possible combinations are handled.
3. The algorithm is not only useful for detecting alignments, but can also detect motifs dotting the CA space.

Results

An algorithm embodying the invention (presented in the Appendix, and for convenience referred to as "P-algorithm") was tested with various sets of data. The data sets were obtained from the protein data bank of the web site of the Research Collaboratory for Structural Bioinformatics non-profit consortium. To test the P-algorithm with similar proteins and dissimilar proteins, the DALI service for Fold Classification and Structural Alignments (FSSP) was used at the web site of the European Bioinformatics Institute, which is a non-profit academic organization that forms part of the European Molecular Biology Laboratory.

The DALI server provides a percent similarity between two protein structures based on the amino acid sequences. The similarity is a measure of the percent of similar amino acids in the final alignment. The scoring for the P-algorithm uses only the structure information and not any sequence related information.

In the P-algorithm, the best alignment is when the smaller of the two structures is completely aligned with the larger of them. The score for a P-algorithm alignment calculates the percentage of cells that are contributing to the "largest alignment". Largest alignment here is a relative term since the P-algorithm can be configured to detect alignments of any length. The results of all the runs shown below are for alignments that are greater than 5 continuous cells. Since each cell is comprised of 5 amino acids (with an overlap of two), the length of the alignments considered for scoring are greater than 13.

If Nmax be the number of cells (Penta-Peptide Blocks) in the smaller of the two structures, and Nc be the number of cells of the final alignment, then P-algorithm Score=Nmax/Nc.

Run 1—Proteins "ISCU_A" having 288 C-alpha atoms and "IEUD_A" having 306 C-alpha atoms.

Run 2—Proteins "IE6K_A" having 129 C-alpha atoms and "IM5T_A" having 124 C-alpha atoms.

Run 3—Proteins "ID0Z_A" having 310 C-alpha atoms and "IHRK_A" having 423 C-alpha atoms.

Run 4—Proteins "IKGS_A" having 223 C-alpha atoms and "IJFT_A" having 340 C-alpha atoms.

FIGS. 12-15 shows the visual protein structure results of running the algorithm on the different data sets, respectively for Run 1-Run 4. The following table provides a comparison.

TABLE 4

| Run No. | % Similarity (Dali) | Nmax | Nc | Score |
|---|---|---|---|---|
| 1 | 66 | 143 | 87 | 61 |
| 2 | 23 | 61 | 18 | 29 |
| 3 | 26 | 154 | 51 | 33 |
| 4 | 8 | 110 | 11 | 9 |

The P-algorithm compares favorably with the DALI technique.

Computer Hardware

Figure 16:
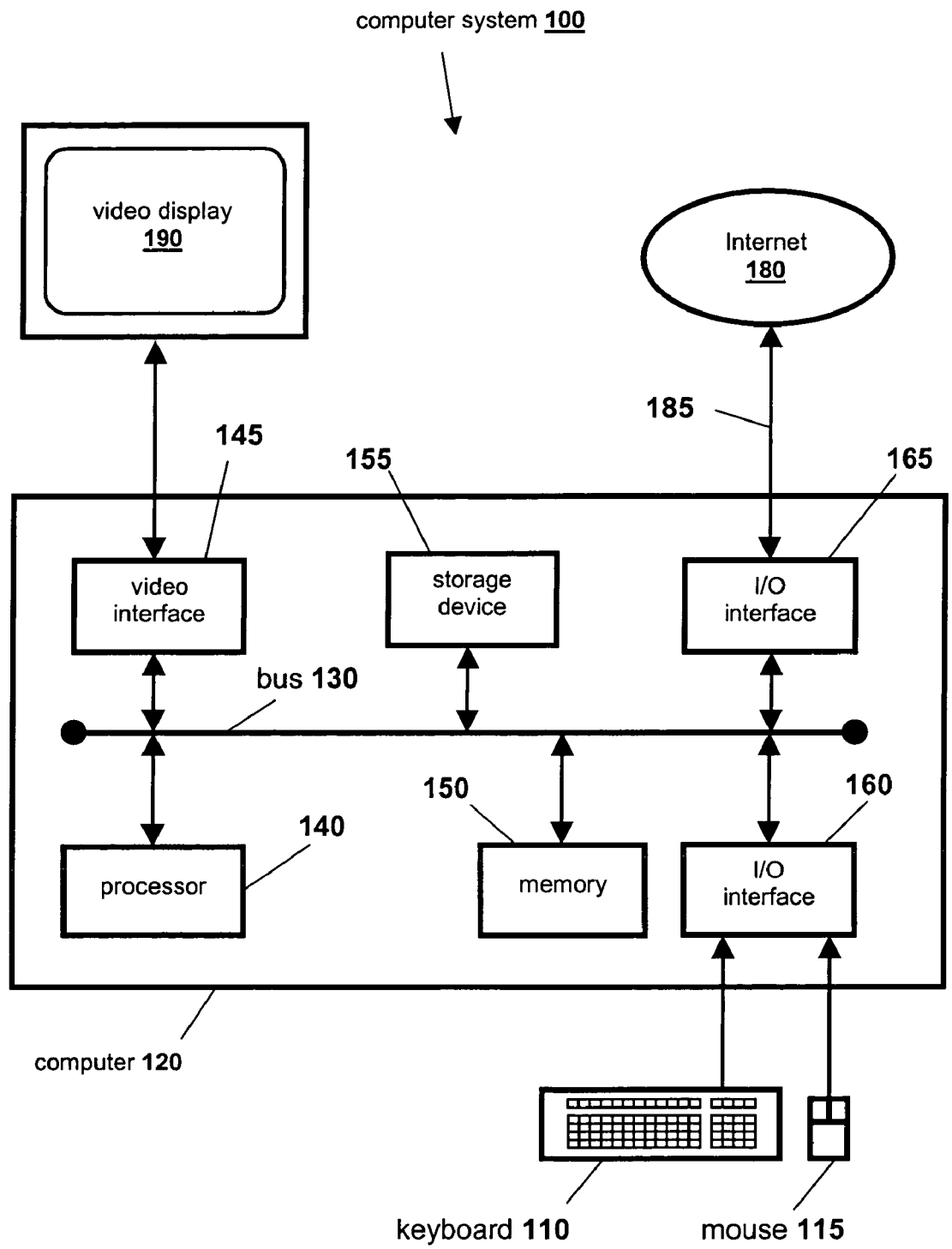
FIG. 16 is a schematic representation of a computer system suitable for performing the techniques described herein.

FIG. 16 is a schematic representation of a computer system 100 of a type that is suitable for executing computer software for protein structure alignment using cellular automata. Computer software, given as pseudocode in the Appendix, executes under a suitable operating system installed on the computer system 100, and may be thought of as comprising various software code means for achieving particular steps.

The components of the computer system 100 include a computer 120, a keyboard 110 and mouse 115, and a video display 190. The computer 120 includes a processor 140, a memory 150, input/output (I/O) interfaces 160, 165, a video interface 145, and a storage device 155.

The processor 140 is a central processing unit (CPU) that executes the operating system and the computer software executing under the operating system. The memory 150 includes random access memory (RAM) and read-only memory (ROM), and is used under direction of the processor 140.

The video interface 145 is connected to video display 190 and provides video signals for display on the video display 190. User input to operate the computer 120 is provided from the keyboard 110 and mouse 115. The storage device 155 can include a disk drive or any other suitable storage medium.

Each of the components of the computer 120 is connected to an internal bus 130 that includes data, address, and control buses, to allow components of the computer 120 to communicate with each other via the bus 130.

The computer system 100 can be connected to one or more other similar computers via a input/output (I/O) interface 165 using a communication channel 185 to a network, represented as the Internet 180.

The computer software may be recorded on a portable storage medium, in which case, the computer software program is accessed by the computer system 100 from the storage device 155. Alternatively, the computer software can be accessed directly from the Internet 180 by the computer 120. In either case, a user can interact with the computer system 100 using the keyboard 110 and mouse 115 to operate the programmed computer software executing on the computer 120.

Other configurations or types of computer systems can be equally well used to execute computer software that assists in implementing the techniques described herein.

CONCLUSION

Various alterations and modifications can be made to the techniques and arrangements described herein, as would be apparent to one skilled in the relevant art.

APPENDIX

Data Structures

The important data structures used in P-algorithm are:

| | | |
|---|---|---|
| C_alpha [id, x, y, z] | | /*C_alpha is a structure consisting of an ID and 3 double values, one each for the x, y, and z co-ordinates.*/ |
| C_alpha_list | | /* C_alpha_list is a list containing objects of type c_alpha. The element at location i is referred as c-alpha-list(i) */ |
| Distance_Matrix | | /* Distance_Matrix is a 2-dimensional (5×5) matrix.*/ |
| Distance_Matrix_list | | /* Distance_Matrix_list is a list containing objects of type Distance_Matrix */ |
| Difference_Matrix | | /* Difference_Matrix is a 2 dimensional matrix*/ |
| CA_GRID | | /* CA_GRID is a 3 dimensional matrix (m×n×2) used to evolve the successive generations of the CA. There are 2 layers of (m×n) matrices.*/ |

The P-Algorithm

```
Start_P-algorithm                    /* begin of program */
{
C_alpha_list c1, c2;
Distance_Matrix_list dm1, dm2;
Global Difference_Matrix dmx;        /*used by other functions*/
```

-continued

```
Global CA_GRID grid;                            /*used by other functions*/
                                                /*read_pdb_file is a function that will read all the records of the
c1=read_pdb_file ("pdbfile1.pdb");              given pdb file and returns a c_alpha_list containing all the c-alpha
c2=read_pdb_file ("pdbfile2.pdb");              atoms as objects of type C_alpha*/
dm1=generate_PPBs (c1, 5);                      /*generate_PPBs is a function that will take in a c_alpha_list and a
dm2=generate_PPBs (c2, 5);                      block-size and will generate a distance_matrix_list with block-size taken
                                                as a parameter */
dmx=generate_difference_matrix (dm1,dm2);       /* generate_difference_matrix takes in two distance matrix
                                                lists (the penta-peptide blocks) and generates the difference
                                                matrix*/
Plot_initial_configuration ( );                 /* Plot_initial_configuration reads the global DMX and fills up the first layer of
                                                (m×n) values of the global grid variable*/
number_of_generations=4;                        /* evolve the initial configuration for 5 generations*/
for i=1;i<number_of_generations;i++
{
    evolveCA ( );                               /* Start a loop starting at generation=I and go on for specified
                                                number_of_generations*/
}
/* At the end of evolving for 5 generations, the first layer of (m×n) cells of the grid contain the live cells signifying the alignment*/
}
End_P-algorithm
```

Pseudo-Code for the Various Functions Used in P-Algorithm

```
function generate_PPBs(c_alpha_list ca, integer block_size)
{
/* Since the block size for Pelican is 5, in order that each PPB contains 5 c-alphas with an overlap of 2, the number of c-alphas should be odd. This
part of the code checks for this condition and adds a dummy c-alpha in the end with the same value as the last c-alpha that was in the list */
number_of_ca = Length(ca); /*Length( ) returns the number of elements in the list*/
if number_of_ca is odd
{
ca_dummy=ca(number_of_ca);
ca(number_of_ca+1)= ca_dummy;
}
Distance_Matrix_list dm = new Distance_Matrix_list( );
```

/* a c-alpha-list of size 'm' where m is odd and with a blocksize=5 will generate blocks */ $\left(\dfrac{m-1}{2}\right)-1$

```
number_of_ppbs=((m-1)/2)-1;
for i=1;i< number_of_ppbs;i++
{
        start_index=2*i-1;         /*for all the ppb indices, generate the start_index of the list and the
        end_index=start_index+4;   end_index, and then call a function that will generate the
                                   distance_matrix for this start_index and end_index*/
        dm(i)=make_distance_matrix(ca(start_index:end_index))
                                   /* ca(start_index:end_index)) means extract all elements in the list starting from
                                   start_index to end_index)*/
}
function make_distance_matrix(c_alpha_list ca)
{
        number_of_c_alphas = length(ca);
        Difference_Matrix dm(5,5);
        for i=1;i< number_of_c_alphas;i++
            {
                for j=1;j< number_of_c_alphas;j++
                    {
                        dm(i,j)=sqrt((ca(j).x-ca(i).x)^2+
                                      (ca(j).y-ca(i).y)^2+
                                      (ca(j).z-ca(i).z)^2);
                    }
            }
}
function generate_difference_matrix(Distance_Matrix_list dm1,
Distance_Matrix_list dm2)
{
        m=length(dm1);
        n=length(dm2);
        for i=1;i<m;i++
            {
                for j=1;j<n;j++
                    {
                        dmx (i,j)=sum(abs(dm1(:,:)-dm2(:,:)));
```

-continued

```
                /*sum(abs(dm1(:,:)-dm2(:,:))) will extract all elements of dm1 and dm2 one by one and take
                their absolute difference and sum them up*/
            }
        }
}
function Plot_initial_configuration( )
{
set all value in the first layer of grid to 0;
m=number_of_rows(dmx);
n=number_of_columns(dmx);
for i=1;i<m;i++
        {
            for j=1;j<n;j++
            {
                get the element at dmx(i,j);
                get all neighbors (9-square neighbor) of the element;
                find the least value among the neighbors;
                row= row corresponding to the least value neighbor;
                col= col corresponding to the least value neighbor;
                [grid(row,col,1)]=1;
            }
        }
}
function evolve( )
{
    m=number_of_rows(dmx);
        n=number_of_columns(dmx);
for i=1;i<m;i++
        {
            for j=1;j<n;j++
            {
                if grid(i,j,l) is alive
                {
                        get the cross neighbors of the cell at
                        grid(i,j,l)
                        if cross neighbors cells
                        [c7,c5,c3,c1]=0 1 0 1
                        then grid(i,j,2)=1;
                        else if cross neighbors cells
                        [c7,c5,c3,c1]=0 1 1 1
                        then grid(i,j,2)=1;
                        else if cross neighbors cells
                        [c7,c5,c3,c1]=1 0 1 0
                        then grid(i,j,2)=2;
                        else if cross neighbors cells
                        [c7,c5,c3,c1]=1 0 1 1
                        then grid(i,j,2)=2;
                        else if cross neighbors cells
                        [c7,c5,c3,c1]=1 1 0 1
                        then grid(i,j,2)=1;
                        else if cross neighbors cells
                        [c7,c5,c3,c1]=1 1 1 0
                        then grid(i,j,2)=2;
                        else if cross neighbors cells
                        [c7,c5,c3,c1]=1 1 1 1
                        then grid(i,j,2)=3;
                        else
                        grid(i,j,2)=0;
                }
            }
        }
/*copy all values of grid layer 2 to grid layer 1*/
grid(:,:,1)=grid(:,:,2);
}
```

What is claimed is:

1. A method for detecting alignments for protein sequences, the method comprising:

generating respective data sets for two protein sequences, wherein such a data set represents protein blocks having n successive C-alpha atoms of a primary amino acid sequence;

determining, for the data sets, respective first and second matrices of distances of protein atoms from said C-alpha atoms, wherein the distance matrices have respective distance matrix elements, the distance matrix elements having respective numerical values;

determining a difference matrix from said first and second distance matrices, wherein the difference matrix has numerical difference matrix elements; and determining alignments for the protein sequences based upon the difference matrix, wherein determining the alignments includes the steps of:

forming, by a processor of a suitably programmed computer system, a model having a set of logical cells in a memory of the computer system, the cells having respective binary logical states, wherein the cells of the model form a matrix such that for each of the difference matrix elements there is a corresponding one of the cells of the model; and performing iterations in which the states of the cells in the memory are selectively altered, including ones of the cells being altered responsive to binary logic states of respectively neighboring ones of the cells.

2. The method of claim 1, wherein the logical states include an alive state and a dead state, forming the model includes initially setting ones of the cells to the alive state, and performing iterations includes converting ones of the cells from the alive state to the dead state.

3. The method of claim 2, each of the difference matrix elements having a respective set of neighboring ones of the elements, wherein in the initially setting of ones of the cells to the alive state such a cell is selected to be set to the alive state responsive to the value of the cell's corresponding difference matrix element relative to the values of the neighbors of the difference matrix element.

4. The method of claim 3, wherein the cells of the model have respective sets of neighboring ones of the model cells, and wherein such a cell that was initially set to the alive state is selected in one of the iterations to remain in the alive state responsive to whether certain neighboring ones of the model cells are in the alive state.

5. The method of claim 4, wherein the certain neighboring ones of the model cells are diagonally adjacent to the cell selected to remain in the alive state.

6. The method of claim 1, wherein ones of said protein blocks overlap adjacent ones of the protein blocks.

7. The method of claim 1, wherein n is a value from 1 to 10.

8. The method of claim 1, wherein n is 5.

9. A system for detecting protein sequence alignments for protein sequences, wherein the system comprises:
   a processor; and
   a memory having a computer program stored therein, wherein the processor is suitably programmed by and operable with the computer program to generate respective data sets for two protein sequences, wherein such a data set represents protein blocks having n successive C-alpha atoms of a primary amino acid sequence;
   wherein the processor is further suitably programmed by and operable with the computer program to determine, for the data sets, respective first and second matrices of distances of protein atoms from said C-alpha atoms, wherein the distance matrices have respective distance matrix elements, the distance matrix elements having respective numerical values; and
   wherein the processor is further suitably programmed by and operable with the computer program to determine a difference matrix from said first and second distance matrices, wherein the difference matrix has numerical difference matrix elements; and determine alignments for the protein sequences based upon the difference matrix, wherein determining the alignments includes i) forming a model having a set of logical cells, the cells having respective binary logical states, wherein the cells of the model form a matrix such that for each of the difference matrix elements there is a corresponding one of the cells of the model and ii) performing iterations in which the states of the cells are selectively altered, including ones of the cells being altered responsive to binary logic states of respectively neighboring ones of the cells.

10. The system of claim 9, wherein the logical states include an alive state and a dead state, forming the model includes initially setting ones of the cells to the alive state, and performing iterations includes converting ones of the cells from the alive state to the dead state.

11. The system of claim 10, each of the difference matrix elements having a respective set of neighboring ones of the elements, wherein in the initially setting of ones of the cells to the alive state such a cell is selected to be set to the alive state responsive to the value of the cell's corresponding difference matrix element relative to the values of the neighbors of the difference matrix element.

12. The system of claim 11, wherein the cells of the model have respective sets of neighboring ones of the model cells, and wherein such a cell that was initially set to the alive state is selected in one of the iterations to remain in the alive state responsive to whether certain neighboring ones of the model cells are in the alive state.

13. The system of claim 12, wherein the certain neighboring ones of the model cells are diagonally adjacent to the cell selected to remain in the alive state.

14. The system of claim 9, wherein ones of said protein blocks overlap adjacent ones of the protein blocks.

15. The system of claim 9, wherein n is a value from 1 to 10.

16. The system of claim 9, wherein n is 5.

17. A computer program product for detecting alignments for protein sequences, the computer program product comprising a computer program on a storage medium, said computer program including code means for performing the steps of:
   generating respective data sets for two protein sequences, wherein such a data set represents protein blocks having n successive C-alpha atoms of a primary amino acid sequence;
   determining, for the data sets, respective first and second matrices of distances of protein atoms from said C-alpha atoms, wherein the distance matrices have respective distance matrix elements, the distance matrix elements having respective numerical values;
   determining a difference matrix from said first and second distance matrices, wherein the difference matrix has numerical difference matrix elements; and
   determining alignments for the protein sequences based upon the difference matrix, wherein determining the alignments includes the steps of:
   forming, by a processor of a suitably programmed computer system, a model having a set of logical cells in a memory of the computer system, the cells having respective binary logical states, wherein the cells of the model form a matrix such that for each of the difference matrix elements there is a corresponding one of the cells of the model; and
   performing iterations in which the states of the cells in the memory are selectively altered, including ones of the cells being altered responsive to binary logic states of respectively neighboring ones of the cells.

18. The computer program product of claim 17, wherein the logical states include an alive state and a dead state, forming the model includes initially setting ones of the cells to the alive state, and performing iterations includes converting ones of the cells from the alive state to the dead state.

19. The computer program product of claim 18, each of the difference matrix elements having a respective set of neighboring ones of the elements, wherein in the initially setting of ones of the cells to the alive state such a cell is selected to be set to the alive state responsive to the value of the cell's corresponding difference matrix element relative to the values of the neighbors of the difference matrix element.

20. The computer program product of claim 19, wherein the cells of the model have respective sets of neighboring ones of the model cells, and wherein such a cell that was initially set to the alive state is selected in one of the iterations to remain in the alive state responsive to whether certain neighboring ones of the model cells are in the alive state.

21. The computer program product of claim 20, wherein the certain neighboring ones of the model cells are diagonally adjacent to the cell selected to remain in the alive state.

22. The computer program product of claim 17, wherein ones of said protein blocks overlap adjacent ones of the protein blocks.

23. The computer program product of claim 17, wherein n is a value from 1 to 10.

24. The computer program product of claim 17, wherein n is 5.

* * * * *